United States Patent [19]

Hall et al.

[11] Patent Number: 4,925,832

[45] Date of Patent: May 15, 1990

[54] SILVER HALIDE PHOTOGRAPHIC LIGHT-SENSITIVE SYSTEMS

[75] Inventors: Kevin P. Hall, Essex; Andrew W. Mott, Bishops Stortford, both of England

[73] Assignee: Minnesota Mining and Manufacturing Company, St. Paul, Minn.

[21] Appl. No.: 264,988

[22] Filed: Oct. 31, 1988

Related U.S. Application Data

[62] Division of Ser. No. 68,146, Jun. 29, 1987, Pat. No. 4,798,780.

[30] Foreign Application Priority Data

Jul. 16, 1986 [GB] United Kingdom ............... 8617335

[51] Int. Cl.$^5$ .................. C07C 109/04; C07C 109/10
[52] U.S. Cl. .................................... 564/149; 564/150; 430/264; 430/268; 430/598; 430/599; 430/949
[58] Field of Search ................ 564/149, 150; 514/615

[56] References Cited

U.S. PATENT DOCUMENTS

| | | | |
|---|---|---|---|
| 3,162,680 | 12/1964 | Biel | 564/149 |
| 4,168,977 | 9/1979 | Takada et al. | 96/63 |
| 4,224,401 | 9/1980 | Takada et al. | 430/437 |
| 4,385,108 | 5/1983 | Takagi et al. | 430/264 |
| 4,447,522 | 5/1984 | Hirano | 430/405 |

FOREIGN PATENT DOCUMENTS 0053369 1/1967 Fed. Rep. of Germany ...... 564/149

OTHER PUBLICATIONS

Zeller et al., *Amino Acid and Fatty Acid Hydraziodes: Chemistry and Action on Monoamine Oxidase;* Annals of New York Academy of Science, (vol. 80, Cert. 3, pp. 555-567), Sep. 17, 1959.

*Primary Examiner*—Richard L. Raymond
*Assistant Examiner*—K. Konstas
*Attorney, Agent, or Firm*—Donald M. Sell; Walter N. Kirn; Mark A. Litman

[57] ABSTRACT

A silver halide photographic light sensitive emulsion containing a hydrazine of the general formula $$R^3\text{-}NR^4\text{-}NR^5\text{-}G\text{-}X \qquad (I)$$

in which
$R^3$ represents an aryl group,
one of $R^4$ and $R^5$ is a hydrogen and the other is selected from hydrogen, aryl sulphonyl and trifluoroacetyl,
G represents carbonyl, sulphonyl, sulphoxy, phosphoryl or an N-substituted or unsubstituted imino group and X is a moiety such that at a pH in the range of 9.5 to 12.5 in the presence of an oxidized hydroquinone a cyclization reaction takes place cleaving the moiety -G-X from the remainder of the molecule and forming a cyclic structure comprising atoms of the moiety -G-X.

9 Claims, No Drawings

SILVER HALIDE PHOTOGRAPHIC LIGHT-SENSITIVE SYSTEMS

This is a division of application Ser. No. 068,146 filed June 29, 1987, now Pat. No. 4,798,780.

FIELD OF INVENTION

This invention relates to silver halide photographic light-sensitive systems and in particular to photographic light-sensitive materials containing particular hydrazines in the emulsion providing ultrahigh contrast upon exposure and development.

BACKGROUND TO THE INVENTION

Hydrazines find a variety of uses in silver halide photography. They have been used in negative working surface latent image forming silver halide emulsions to increase speed and/or contrast. They have been used in direct positive internal latent image forming emulsions as nucleating agents.

Hydrazines may also be used for internal latent image direct positive emulsions such as those described in U.S. Pat. No. 3,227,552 and reviewed in Research Disclosure No. 235 (1983) item 23510.

The most efficient hydrazines employed in silver halide photographic systems employ a combination of substituents to balance activity and stability. The stability of hydrazines is increased by attaching directly to one of the nitrogen atoms a tertiary carbon atom, such as the carbon atom of an aromatic ring. The art has long recognized that the activity of these stabilised hydrazines can be advantageously modified by the direct attachment of an acyl group to the remaining nitrogen atom. Thus, the most commonly employed hydrazines are arylhydrazides.

Silver halide emulsions and/or developers containing hydrazines are disclosed, for example, in U.S. Pat. Nos. 2,419,975, 2,563,785, 3,227,552, 3,386,831, 3,730,727, 4,030,925, 4,031,127, 4,080,207, 4,168,977, 4,224,401, 4,243,739, 4,245,037, 4,255,511, 4,266,013, 4,272,614, 4,276,364, 4,323,643, 4,478,928 and 4,560,638 and U.K. Patent Specifications Nos. 1560005, 1579956, 2034908A and 2066492B.

In particular U.S. Pat. No. 2,419,975 discloses that high-contrast negative images are obtained by the addition of hydrazine compounds. This patent describes that extremely high-contrast photographic characteristics, such as a gamma ($\gamma$) of more than 10, can be obtained by adding a hydrazine compound to a silver chlorobromide emulsion and developing at a pH as high as 12.8. However, the strongly alkaline developer having a pH of nearly 13 is susceptible to air oxidation and is too unstable to be stored or used for long periods.

U.S. Pat. No. 4,168,977 discloses the use of a hydrazine of the formula:

$$R^1NHNHCHO$$

in which $R^1$ represents an aryl group, in combination with silver chlorobromide or silver chlorobromoiodide emulsions. This combination is capable of functioning at a lower pH than the hydrazines of U.S. Pat. No. 2,419,975 and a pH of 11.5 is exemplified.

U.S. Pat. No. 4,224,401 discloses the use of a hydrazine of the formula:

$$R^1NHNHCOR^2$$

in which $R^1$ is an aryl group and $R^2$ is a hydrogen atom, $C_1$ to $C_3$ alkyl or phenyl optionally substituted with substitutents which are preferably electron withdrawing, in combination with silver bromide or silver iodobromide emulsions. This combination is also functional at a pH lower than that disclosed in U.S. Pat. No. 2,419,975 and a pH of 11.5 is exemplified when $R^2$ is hydrogen.

There is a need to provide alternative hydrazines which allow a lowering of pH to reduce adverse effects incurred by aerial oxidation of the developer.

The present invention provides an alternative group of hydrazines which may be employed in silver halide emulsions to provide ultrahigh contrast materials which may be developed at a pH below 12.5.

SUMMARY OF THE INVENTION

According to the present invention there is provided a silver halide photographic light sensitive emulsion containing a hydrazine of the general formula:

$$R^3-NR^4-NR^5-G-X \quad (I)$$

in which:

$R^3$ represents an aryl group, one of $R^4$ and $R^5$ is a hydrogen and the other is selected from hydrogen, aryl sulphonyl and trifluoroacetyl, G represents carbonyl, sulphonyl, sulphoxy, phosphoryl or an N-substituted or unsubstituted imino group and X is a moiety such that at a pH in the range of 9.5 to 12.5 in the presence of an oxidised hydroquinone a cyclisation reaction takes place cleaving the moiety -G-X from the remainder of the molecule and forming a cyclic structure comprising atoms of the moiety -G-X.

It has been found that the particular class of hydrazines used in the invention provide advantageous properties compared to the hydrazines previously used in the art. In particular, the hydrazines used in the invention provide unexpectedly higher contrast photographic characteristics when developed in a developer having relatively low pH, eg. pH 11, compared to developers used with prior art hydrazines at the same pH. The compounds of the present invention also provide superior latitude in development pH over prior art compounds. This is particularly important because pH changes occur during aerial oxidation of photographic developers in the processing machine. The invention also unexpectedly provides superior photolithographic dot quality to compounds in prior art with an absence of processing streaks.

It is known that the diffusibility and solubility of the hydrazine compounds can affect the quality of the high contrast film produced. It has been shown that in a series of alkyl substituted ureido formylphenylhydrazines increasing the alkyl chain length up to 6 carbon atoms on the adjacent nitrogen atom gives increasing activity because shorter chain lengths are washed out of the coating more rapidly. Compounds with alkyl chains longer than 6 carbon atoms give decreased activity because of their decreased mobility and solubility. For a relatively mobile and soluble hydrazine, such a formylphenylhydrazine, problems can occur on processing. The active fogging agent may be swept out of the developing areas e.g. half tone dots, by the passage of the developer solution causing processing streaks. The hydrazines of the present invention provide excellent dot quality and reduction of processing streaks.

It is believed that the hydrazines used in the invention have a different mechanism of action compared to hydrazines previously used in the art. It is postulated that the active fogging agent derived from hydrazines is phenyldiimine and this is formed from the prior art hydrazines by a two stage reaction scheme, firstly an oxidation reaction with oxidised developer and thereafter an hydrolysis reaction. It is believed that the hydrolysis reaction requires high pH.

The hydrazines of the invention are selected to yield an aryldiimine (eg. phenyldiimine) active fogging agent without hydrolysis. Instead the hydrazines are believed to undergo an intramolecular nucleophilic displacement reaction to form aryldiimine and a cyclic structure derived from the moiety -G-X. This reaction proceeds under basic conditions, generally within the pH range 9.5 to 12.5.

The types of substituents for the moiety -G-X capable of a cyclising reaction will readily be appreciated. Generally X will be represented by the formula

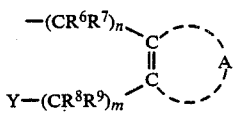

in which:
$R^6$ to $R^9$ are independently selected from H, alkyl of up to 12 carbon atoms or aryl of up to 12 carbon atoms,
A represents the necessary atoms to complete a 5- or 6-membered ring which may possess substituents,
Y represents OH, SH or $NHR^{10}$ in which $R^{10}$ is H, alkyl of up to 12 carbon atoms, or aryl of up to 12 carbon atoms
n is 0 or 1, m is 0 or 1 and (n+m) is 1 or 2.

Thus, preferred compounds for use in the invention are of the general formula

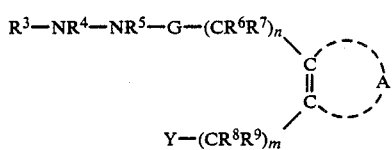

in which: $R^3$ to $R^9$, G, A, Y, m and n are as defined above.

Preferably A represents the necessary atoms to complete a benzene ring.

Preferably G represents C=O.

A particularly preferred structure for the moiety -GX is:

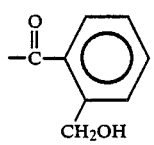

The moiety -G-X is capable of cyclising to form a 5 or 6 membered ring eg. lactone or lactam. Specific examples are

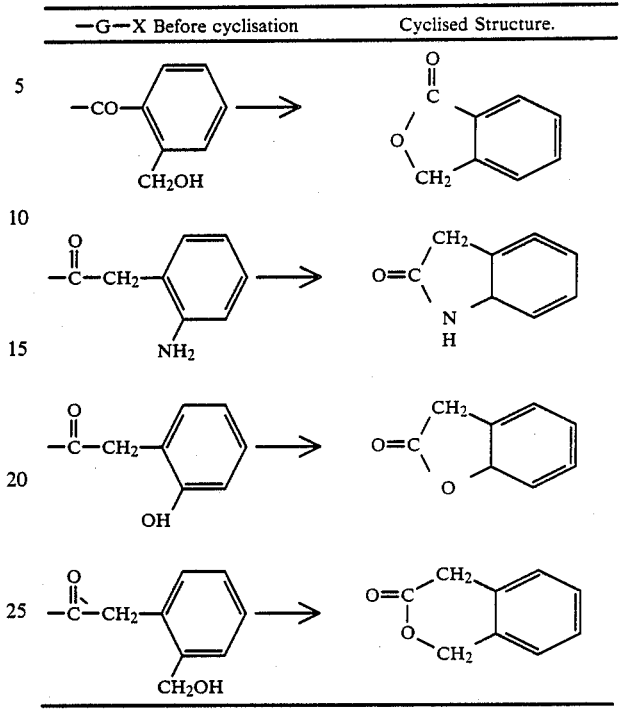

It will be noted that the functional moiety on the phenyl is electron donating. The phenyl ring may optionally possess other substituents. Known hydrazines used in the prior art, e.g. U.S. Pat. No. 4,224,401, have possessed a similar structure with a moiety -G-X of the formula $—COR^{20}$ in which $R^{20}$ is hydrogen, alkyl, phenyl or phenyl substituted with electron withdrawing substituents. Such groups are not capable of cyclisation under basic conditions.

When any of the groups $R^6$ to $R^9$ are alkyl the alkyl group may be straight chained or branched and generally contains up to 12 carbon atoms, preferably no more than 3 carbon atoms. When any of the groups $R^6$ to $R^9$ are aryl the groups generally contain from 5 to 12 carbon atoms and may optionally include substituents such as alkyl, alkoxy, etc. Preferably $R^6$ to $R^9$ are hydrogen.

$R^3$ is aryl, generally a monocyclic or bicyclic aryl group. An example of a monocyclic aryl group is a phenyl group and a suitable example of a bicyclic aryl group is a naphthyl group. The aryl group may be substituted with one or more substituents which are not electron-attracting, such as alkyl groups having 1 to 20 carbon atoms (which may be straight or branched chained, e.g., methyl, ethyl, propyl, iso-propyl, n-butyl, iso-butyl, n-octyl, n-hexyl, tert-octyl, n-decyl, n-dodecyl, etc.), aralkyl groups having 1 to 3 carbon atoms in the alkyl moiety thereof (e.g., benzyl, phenethyl, etc.), alkoxy groups having 1 to 20 carbon atoms (in which the alkyl moiety may be straight or branched chain, e.g., methoxy, ethoxy, 2-methylpropoxy, etc.), amino groups which are mono- or disubstituted with alkyl groups having 1 to 20 carbon atoms, aliphatic acylamino groups having 2 to 21 carbon atoms or aromatic acylamino groups (e.g., acetylamino, octynylamino, benzoylamino, dimethylamino, etc.), etc.

Preferably $R^3$ represents

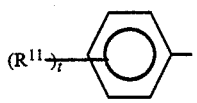

in which:

t is 0 or an integer of 1 to 3, and $R^{11}$ represents alkyl of up to 12 carbon atoms, preferably 1 to 5 carbon atoms, alkoxy of up to 12 carbon atoms, halogen or $NHCOR^{10}$ in which $R^{10}$ is as defined above.

A preferred class of compounds for use in the invention has the formula

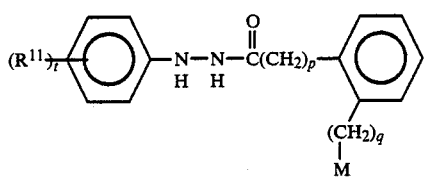

in which:

p and q are independently selected from 0 or 1 such that (p+q)=1

$R^{11}$ is as defined above

M is $NH_2$ or OH

A compound of the above formula in which M is OH, p is zero and t is zero is known; the remaining compounds are novel and form a further aspect of this invention.

Particularly preferred compounds of the invention are of the formula:

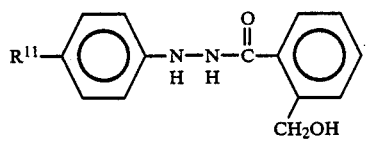

in which: $R^{11}$ is as defined above.

A preferred hydrazine for use in the invention is 1-(2'-hydroxymethylbenzoyl)-2-phenyl hydrazine. This compound after oxidation may readily undergo the following intramolecular nucleophilic displacement to form phenyl diimine and a lactone:

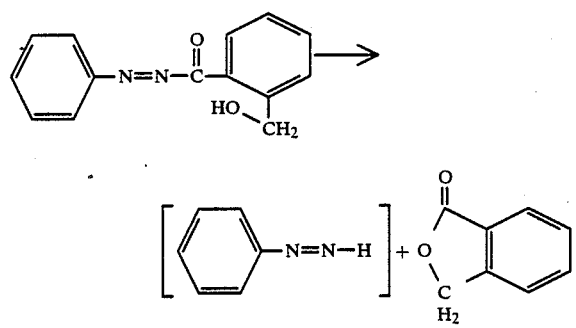

Further preferred hydrazines for use in the invention are of the formula:

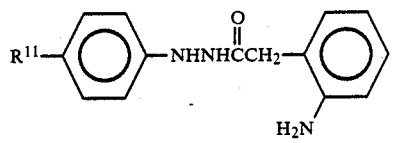

in which: $R^{11}$ is as defined above.

Hydrazines useful in the present invention which undergo a cyclising reaction under processing conditions may be determined by a simple test as follows:

Dissolve 0.1 g of the compound under test in the minimum amount of methanol. Add this to 50 ml of an aqueous solution which has be adjusted to pH 11.5 with sodium hydroxide. If an initial pH drop occurs, readjust to pH 11.5 with sodium hydroxide and bubble oxygen through the solution, at room temperature, for a period of up to 30 minutes whilst maintaining a pH of 11.5. 30 minutes is considered to be the maximum time period acceptable for a photographic processing stage. The solution is adjusted to pH 6 with dilute sulphuric acid at any time up to 30 minutes and the cyclized lactone or lactam, if present, can then be isolated by an appropriate analytical technique.

Where the cyclized product is soluble in ether, isolation can be achieved by saturating the solution with sodium chloride and extracting it with ether.

The lactone or lactam can be identified in the ether soluble residue, from the specific position of its carbonyl peak in the infrared spectrum, obtained by well known procedures.

The hydrazines may be added to the silver halide photographic emulsion at any desired period from the initiation of chemical ripening to before coating, but it is preferred to add the compound after finishing chemical ripening. It is particularly preferred to add the compound to a coating composition prepared for coating.

It is preferred that the hydrazine of this invention be incorporated in an amount of from $10^{-6}$ mol to $10^{-1}$ mol, and preferably from $10^{-5}$ mol to $2 \times 10^{-2}$ mol per mol of silver halide, but it is desirable to select the optimum amount of the compound according to the grain size of silver halide emulsion, the halogen composition, the manner and extent of chemical sensitization, and the kind of anti foggant compounds. The most appropriate compound and amount thereof for a particular use can be easily selected by general tests well known to persons skilled in the art.

It is preferred that silver halide grains used for at least one silver halide emulsion layer in this invention be of substantially surface latent image type.

Any light sensitive silver halide may be used in this invention e.g., silver chloride, silver chlorobromide, silver iodochlorobromide, silver bromide, silver iodochloride and silver iodobromide can be used. In the case of using silver iodobromide or silver iodochlorobromide, it is preferred that the content of silver iodide not be more than 10 mole percent. Since in the material of this invention a wide range of silver halides can be used, it is possible to obtain a very high sensitivity as compared with a process using a conventional "lith" type development. The preferred silver halide for use in the invention is silver chlorobromoiodide.

The silver halide photographic emulsions used in this invention can be prepared by the processes described in, for example, P. Glafkides, Chimie et Physique Photographique (published 1967 by Paul Montel); G. F. Duffin, Photographic Emulsion Chemistry, (published 1966, by the Focal Press); and V. L. Zelikman et al., Making and coating Photographic Emulsions (published 1964 by The Focal Press). That is, the silver halide emulsions may be prepared by an acid process, a neutral process, an ammonia process, etc. The silver halide may be precipitated by a single jet mixing process, a simultaneous mixing process, or a combination thereof. Also, a so-called reverse mixing method, wherein silver halide grains are formed in the presence of silver ion can be employed. In an embodiment of the simultaneous mixing method, a method of maintaining the pAg of the liquid phase wherein silver halide is formed at a constant value, that is, a so-called controlled double jet method, can be employed. According to the method, a silver halide emulsion having regular crystal form and almost uniform grain size is obtained.

Silver halide grains in the silver halide photographic emulsion used in this invention may have a relatively broad grain size distribution, but it is preferred that the emulsion has a narrow grain size distribution. Alternatively a mixture of two emulsions may be employed as described in British Patent Application No. 8516934, e.g. a coarse grain silver halide emulsion having an average grain size of from 0.1 to 4 microns and a fine grain silver halide emulsion having an average grain volume of less than one half that of the coarse grain emulsion.

Silver halide grains used in this invention are preferably fine grains (e.g., less than 0.7 microns) but since the noohydrazines will provide a high contrast image even if the mean grain size is large and sufficiently improves the dot qualities, silver halide emulsions having large grains (e.g., larger than 0.7 microns) can be used.

The silver halide grains in the silver halide photographic emulsions may be regular crystals such as cubic or octahedral crystals, or irregular crystals such as spherical or plate-like crystals, as well as composite forms of fixed crystals thereof. They may be mixture of various crystal form grains.

The silver halide grain may have a uniform phase throughout the inside and surface layer thereof or may be different in phase between the inside and the surface layer (e.g., a shell-core structure). Moveover, two or more sorts of silver halide emulsions prepared separately may be used as a mixture thereof.

As the binder or protective colloid for the silver halide emulsions, gelatin is advantageously used but other hydrophilic colloids can be also used. For example, gelatin derivatives, graft polymers of gelatin and other polymers, albumin, casein, etc,; cellulose derivatives such as hydroxyethyl cellulose, carboxymethyl cellulose, cellulose sulphate ester, etc,; sugar derivatives such as sodium alginate, a starch derivative, etc.; and various sorts of synthetic hydrophilic polymers as homopolymers or copolymers, such as polyvinyl alcohol, polyvinyl alcohol partial acetal, poly-N-vinylpyrrolidone, polyacrylic acid, polymethacrylic acid, polyacrylamide, polyvinyl imidazole, polyvinyl pyrazole, etc., can be used.

As the gelatin, limed gelatin and acid-processed gelatin may be used, as well as a gelatin hydrolyzed product and gelatin enzyme-decomposition product may be also used. Examples of the gelatin derivatives used in this invention are the products obtained by reacting gelatin and various compounds such as acid halide, acid anhydride, isocyanate, bromoacetic acid, alkanesultones, vinylsulphonimides, maleimide compounds, polyalkylene oxides, epoxy compounds, etc. Practical examples of these materials are described in U.S. Pat. Nos. 2,614,928, 3,134,945, 3,186,846, 3,312,553, British Pat. Nos. 861414, 1033189 and 1005784 and Japanese Patent Publication No. 26845/67.

Examples of gelatin graft polymers include those prepared by grafting to gelatin a homopolymer or copolymer of a vinylic monomer such as acrylic acid, methacrylic acid, the derivative thereof such as the ester or amide, acrylonitrile, styrene, etc. In particular, a graft polymer of gelatin and a polymer having a compatibility with gelatin to some extent, such as acrylic acid, methacrylic acid, acrylamide, methacrylamide, hydroxyalkylmethacrylate, etc., is preferred. Such graft polymers are described in U.S. Pat. Nos. 2,763,625, 2,831,767 and 2,956,884. Typical examples of the synthetic hydrophilic polymer are described in West German Patent Application (OLS) No. 2312708 U.S. Pat. Nos. 3,620,751 and 3,879,205 and Japanese Patent Publication No. 7561/68.

It is preferred that the silver halide emulsion used in this invention does not contain more than 250 g of binder per mol of silver halide. When the silver halide emulsion contains a binder in an amount not over 250 g per mol of silver halide, extremely high contrast photographic characteristics which are the object of this invention can be more easily obtained.

After forming a precipitate or after physical ripening, soluble salts formed are usually removed from the silver halide emulsion. For this purpose, the well known noodle washing method, or a flocculation method utilizing an inorganic salt composed of a polyvalent anion, such as sodium sulphate, an anionic surface active agent, an anionic polymer (e.g. polystyrenesulphonic acid), or a gelatin derivative (e.g. aliphatic-acylated gelatin, aromatic-acylated gelatin, aromatic-carbamolyated gelatin etc.) may be used. The step of removing soluble salts may be omitted.

The silver halide emulsions used in this invention need not be chemically sensitized, but preferably are chemically sensitized. As methods for chemically sensitizing silver halide emulsions, known sulphur sensitization, reduction sensitization, and noble metal sensitization methods can be used, either solely or in combination. These sensitization methods are described in the aforesaid books by Glafkides and Zelikman et al. as well as Die Grundlagen der Photographischen Prozesse mit Silberhalogeniden, edited by H. Frieser (Akademische Verlagsgesellschaft, 1968).

Of the noble metal sensitization methods, a gold sensitization method is typical and uses gold compounds, in particular gold complexes. Complexes of noble metals other than gold, such a platinum, palladium, iridium, etc., may be also used. Preferred examples thereof are described in U.S. Pat. No. 2,448,060 and British Pat. No. 618061.

Examples of sulphur sensitizers useful for sulphur sensitization include sulphur compounds contained in gelatin as well as various sulphur compounds such as thiosulphates, thioureas, thiazoles, rhodanines, etc. Preferred examples of sulphur sensitizers are described in U.S. Pat. Nos. 1,574,944, 2,278,947, 2,410,689, 2,728,668, 3,501,313 and 3,656,955.

Examples of reduction sensitizers useful in this invention include stannous salts, amines, formamidinesulphinic acid, silane compounds, etc. Practical examples of them are described in U.S. Pat. Nos. 2,487,850, 2,518,698, 2,983,609, 2,983,610 and 2,694,637.

The light-sensitive materials of this invention may contain various other additives known in the art e.g., spectral sensitizers, hardeners, stabilizers etc..

In the process of this invention, the image-exposed silver halide photographic light-sensitive materials can be processed by using a stable developing solution to obtain a high-contrast image and it is unnecessary to process said photographic light-sensitive materials by unstable lithographic developers.

According to the purpose, development processing forming silver image only (black-and-white photographic processing) or color photographic processing including development processing forming dye images can be employed. The processing temperature is usually from 18° C. to 50° C.

Suitable black-and-white developing agents for use in the invention include 3-pyrazolidones (e.g., 1-phenyl-3-pyrazolidone), aminophenols (e.g., N-methyl-p-aminophenol), 1-phenyl-3-pyrazolines and dihydroxybenzenes (e.g., hydroquinone). It is most preferred that a dihydroxybenzene eg. hydroquinone, is used as the developer, optionally in the presence of one or more other developing agents.

The developer used in this invention generally contains preservatives, alkaline agents, pH buffers, anti-foggants (such as, in particular, nitroindazoles, benzotriazoles, etc.), etc., and further may contain, if necessary, dissolution aids, toning agents, development accelerators, surface active agents (eg. polyalkylene glycols), defoaming agents, water softeners, hardening agents and viscosity-imparting agents.

According to the process of this invention, a gamma higher than 10 can be obtained even when the light-sensitive materials are developed in a developer containing not less than about 0.15 mol/liter of sulphite ion. In the process of this invention the pH of the developer may be above about 9 but is preferably from about 9.5 to 12.3, If the pH of the developer is over 12.3, the developer is unstable even when the concentration of sulphite ion is high and hence it is difficult to maintain stable photographic characteristics for more than three days using such a developer.

A fix solution having a conventional composition may be used. Fixing agents such as thiosulphates, thiocyanates, as well as organic sulphur compounds may be employed.

The invention will further be illustrated by the following Examples.

The hydrazines employed in the Examples are reported in the following Tables 1 and 2.

TABLE 1

| COMPOUND | STRUCTURAL FORMULA |
|---|---|
| 1 | Ph—NHNHCHO |
| 2 | Ph—NHNHCO—Ph |
| 3 | Ph—NHNHCOCH$_2$—C$_6$H$_4$-NH$_2$ |
| 4 | Ph—NHNHCOCH$_2$—Ph |
| 5 | Ph—NHNHCOCH$_2$—C$_6$H$_4$-CH$_2$OH |

TABLE 2

R—C$_6$H$_4$—NH—NH—CO—C$_6$H$_4$—CH$_2$OH

| COMPOUND NO. | R | R POSITION |
|---|---|---|
| 6 | H | — |
| 7 | n-C$_4$H$_9$ | para |
| 8 | n-C$_4$H$_9$O | para |
| 9 | CH$_3$ | para |
| 10 | i-C$_3$H$_7$ | para |
| 11 | C$_2$H$_5$O | para |
| 12 | CH$_3$CONH | para |
| 13 | n-C$_5$H$_{11}$ | para |
| 14 | C$_6$H$_{13}$O | para |
| 15 | CH$_3$, CH$_3$ | 2, 6 |
| 16 | Cl | para |
| 17 | C$_6$H$_{11}$ | para |

EXAMPLE 1

Preparation of Compound 6

1-(2'-hydroxymethylbenzoyl) 2-phenylhydrazine

The method adopted is disclosed in Wislicenus (Berichte 20 401). Phenyl hydrazine (27 ml) and phthalide (33 g) were heated together at 70° to 80° C. for 3 hours. After cooling to 20° C. the solid product was stirred with ether (100 ml) and the product collected by filtration, washed with ether and recrystallised from 2-propanol. Yield 9.6 g (16%) melting point 170°–172° C.

Compounds 7 to 17 were prepared by an analogous route starting from the appropriate substituted phenyl hydrazine.

Each of Compounds 6 to 17 provide a cyclised porduct when subjected to the test described hereinbefore.

EXAMPLE 2

Preparation of Compound 3

1(2'aminophenylacetyl)-2-phenyl hydrazine 2-nitrophenylacetic acid (5 g) was stirred with thionyl chloride (3 ml) at 50° C. for 2 hours. Excess thionyl chloride was removed in vacuo and the crude acid chloride was added to a solution of phenyl hydrazine (2.7 ml) and triethylamine (4 ml) in ether (50 ml) at 0° C. After two hours ethyl acetate (100 ml) was added and the mixture cooled, washed with water, dried (MgSO$_4$) and evaporated. The crude 1(2'nitrophenylacetyl)-2-phenylhydrazine was recrystallised from ethanol/water.

Yield 2.4 g (34%).

This nitro compound was dissolved in methanol and then hydrogenated (10% Pd/C, H$_2$ 100 psi). After removing the catalyst the solution was evaporated and the product purified by column chromatography on silica gel (elution with dichloromethane/methanol 19:1.).

Yield 1.1 g (52%) melting point 63° to 65° C.

EXAMPLE 3

Preparation of Compound 4

1-(2'hydroxyphenylacetyl)-2-phenyl hydrazine

Phenyl hydrazine (0.73 ml) was added to a solution of 2-Coumaranone (1 g) in ether (25 ml) and the mixture stirred for 3 hours. The product was collected by filtration, washed with ether and dried.

Yield 1.5 g (82%) melting point 191°–193° C.

EXAMPLE 4

A silver halide emulsion with a bromide:chloride:iodide ratio of 68:30:2 was prepared by conventional double jet techniques. Conditions were chosen such that an emulsion with a narrow grain size distribution was obtained having an average grain size of 0.2 micron. The emulsion was coagulated and washed in the conventional manner and reconstituted to give a silver ratio of 90 g gelatin per mole of silver. The emulsion was chemically sensitised though this was not critical. A conventional stabiliser was then added.

The emulsion was coated onto polyester base at a silver coating weight of 3.0 gm$^2$ with the following additions: wetting agent (Hostapur), a polyethylene oxide (Brij 58), a green sensitizing dye [anhydro-5,5'-dichloro-9-ethyl-3,3'-bis(3 sulphopropyl)oxacarbocyanine hydroxide sodium salt], a contrast promoting agent (benzhydrol) and a hydrazine derivative. The hydrazines used are reported in Tables 1 and 2 and were added either as a dispersion in gelatin or added to the aqueous emulsion as a solution in an organic solvent.

A gelatin top coat was applied comprising 50 g of gelatin per 1000 g water, wetting agent, matting agent (silica), and a hardener (2-hydoxy--b 4-6-dichloro-1,3,5-triazine).

Samples were individually exposed in a sensitometer to light from a 500 Watt tungsten filament lamp which was attenuated by a 0 to 4 continuous neutral density wedge in contact with the coating. The coatings were developed for 60 seconds at 28° C. in either
(a) Kodak Ultratec developer (a hydroquinone developer commercially available from Kodak) pH=11.5
(b) Kodak Ultratec developer with pH adjusted to 12.0.

The sensitometric data of the samples is reported in Tables 3 and 4 together with a subjective assessment of dot quality on a scale of 1 (poor) to 5 (excellent).

TABLE 3

| | | Ultratec developer pH = 11.5 | | | | | |
|---|---|---|---|---|---|---|---|
| Sample | Compound No. | Amount used mol/mol AgX × $10^{-3}$ | Relative log Sensitivity at 0.1 above fog | Minimum Density | Maximum Density | Contrast | Dot Quality |
| 1. | — | 0 | 1.17 | 0.02 | 3.5 | 3 | 1 |

TABLE 3-continued

| | | Ultratec developer pH = 11.5 | | | | | |
|---|---|---|---|---|---|---|---|
| Sample | Compound No. | Amount used mol/mol AgX × $10^{-3}$ | Relative log Sensitivity at 0.1 above fog | Minimum Density | Maximum Density | Contrast | Dot Quality |
| 2. | 1(comp)* | 8.3 | 1.52 | 0.03 | 4.9 | 14.6 | 3 |
| 3. | 2(comp)* | 8.3 | 1.36 | 0.02 | 4.5 | 4.2 | 1 |
| 4. | 6 | 8.3 | 1.60 | 0.03 | 4.7 | 20 | 5 |
| 5. | 7 | 8.3 | 1.60 | 0.03 | 4.8 | 20 | 5 |
| 6. | 5 | 8.3 | 1.44 | 0.04 | 4.4 | 7.5 | 2 |
| 7. | 3 | 8.3 | 1.48 | 0.03 | 4.5 | 10 | 4 |
| 8. | 4 | 8.3 | 1.45 | 0.02 | 4.8 | 18 | 4 |

*comp = comparison

TABLE 4

| | Ultratec Developer pH = 12 | | | | | |
|---|---|---|---|---|---|---|
| Compound | Amount used mol/mol AgX | Relative log Sensitivity at 0.1 above fog | Minimum Density | Maximum Density | Contrast | Dot Quality |
| 1. | — | 1.19 | 0.03 | 3.5 | 3.2 | 1 |
| 2. | 1 | 8.3 × $10^{-3}$ | 1.90 | 0.04 | 5.0 | 19.5 | 3 |
| 3. | 2 | " | 1.56 | 0.04 | 4.5 | 20 | 3 |
| 4. | 6 | " | * | — | — | — | |
| 5. | 7 | " | * | — | — | — | |
| 6. | 5 | " | 1.64 | 0.04 | 4.7 | 20 | 4 |
| 7. | 3 | " | 1.92 | 0.03 | 4.5 | 20 | 5 |
| 8. | 4 | " | 1.64 | 0.03 | 4.8 | 20 | 5 |

*too fogged to measure

Table 3 indicates that hydrazines 6, 7, 3 and 4 in accordance with the invention are very effective as infectious development agents compared to hydrazines 1 and 2. Table 4 shows that hydrazine 5 also infectiously develops but needs a higher pH to do so.

The compounds of the invention also exhibited higher contrast under the same development conditions compared to the reference compounds. Dot quality was also markedly superior.

EXAMPLE 5

Compound numbers 7 to 17 were individually incorporated into emulsions and exposed as in Example 4 and developed at pH 11.0 in Developer 1 formulation.

| Developer 1 | |
|---|---|
| Water | 1800 g |
| Potassium hydroxide | 195 g |
| Potassium metabisulphite | 124 g |
| Diethylenetriaminepentaacetic acid 5Na | 10 g |
| Pyruvic acid sodium salt | 7.5 g |
| Hydroquinone | 60 g |
| Metol | 5.0 g |
| 5-Methylbenzotriazole | 0.2 g |
| Potassium bromide | 9.25 g |
| Potassium chloride | 2.7 g |
| Phosphoric acid (85%) | 90 g |
| Final volume | 2.0 liters pH 11.0 |

The results are reported in the following Table 5.

TABLE 5

| Compound No. | Relative Speed | Contrast | Dmin | Dmax | |
|---|---|---|---|---|---|
| 7 | 1.53 | 20 | .03 | 5.1 | |
| 8 | 1.7 | 20 | .03 | 5.1 | |
| 9 | 1.7 | 20 | .04 | 5.0 | |
| 10 | 1.87 | 20 | .28 | 5.2 | Pepper |

TABLE 5-continued

| Compound No. | Relative Speed | Contrast | Dmin | Dmax |
|---|---|---|---|---|
| 11 | To fast to measure, pepper fog present | | Fog present | |
| 12 | 1.3 | 20 | 0.04 | 5.2 |
| 13 | 1.57 | 20 | .05 | 5.1 |
| 14 | 1.75 | 20 | .08 | 5.2 |
| 15 | 1.57 | 20 | .04 | 5.3 |

Compounds numbers 10 and 11 were very active compounds and pepper fog was found to be present. These compounds would be expected to be useful in lower activity, lower pH developer formulations.

Compounds numbers 16 and 17 also showed ultra high contrast behaviour when tested as described above.

EXAMPLE 6

To further investigate whether a cyclisation mechanism was operating the ortho and para-hydroxymethylisomers of compound 6 were synthesised and evaluated for high contrast effects. The ortho compound is compound 6; the para compound (Compound No. 18) is of the formula

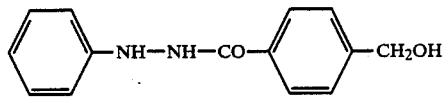

The samples were coated in formulations according to Example 4. Once exposed the films were processed in developer 1 of Example 5 adjusted to pH 11.

It was found that while Compound No. 6 showed the ultra-high contrast behaviour expected, the para isomer gave a very low level of infectious behaviour as shown in the following Table.

TABLE 6

| | Developer 1 pH 11.0 | | | |
|---|---|---|---|---|
| Compound No. | Amount Used mol/mol AgX | Rel. log sensitivity at 0.1 above fog | Maximum density | Contrast |
| 6 | $8.3 \times 10^{-3}$ | 1.20 | 4.0 | 20 |
| 18 | $8.3 \times 10^{-3}$ | 0.94 | 3.4 | 3 |
| 2 | $8.3 \times 10^{-3}$ | 1.05 | 4.0 | 4 |

The level of activity of Compound No. 18 was similar to the unsubstituted benzoyl derivative Compound No. 2. These results suggest that a different mechanism is operating which depends particularly on the position of the hydroxymethyl group. The most logical explanation for this observation is in terms of the cyclisation mechanism given previously.

We claim:

1. A compound of the formula:

TABLE 6

| | Developer 1 pH 11.0 | | | |
|---|---|---|---|---|
| Compound No. | Amount Used mol/mol AgX | Rel. log sensitivity at 0.1 above fog | Maximum density | Contrast |
| 6 | $8.3 \times 10^{-3}$ | 1.20 | 4.0 | 20 |
| 18 | $8.3 \times 10^{-3}$ | 0.94 | 3.4 | 3 |
| 2 | $8.3 \times 10^{-3}$ | 1.05 | 4.0 | 4 | in which:
p and q are independently selected from 0 or 1 such that (p+q)=1 t is 0 through 3
$R^{11}$ is alkyl of up to 12 carbon atoms, alkoxy of up to 12 carbon atoms, halogen or $NHCOR^{10}$ in which $R^{10}$ is H, alkyl of up to 12 carbon atoms, or aryl of up to 12 carbon atoms
M is $NH_2$ or OH
with the proviso that when M is OH and p is zero, t is other than zero.

2. A compound as claimed in claim 1 of the formula

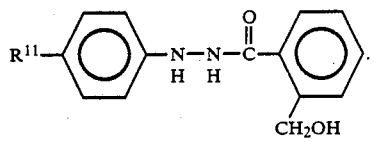

3. A compound according to claim 1 in which the hydrazine is of the formula

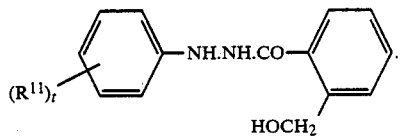

4. The compound of claim 1 which is 1(2'-aminophenylacetyl)-2-phenylhydrazine.

5. A hydrazine compound of the general formula $$R^3\text{-}NR^4\text{-}NR^5\text{-}G\text{-}X \quad (I)$$

in which:
$R^3$ represents an aryl group,
one of $R^4$ and $R^5$ is a hydrogen and the other is selected from hydrogen, aryl sulphonyl and trifluoroacetyl,
G represents carbonyl and
X is a moiety such that at a pH in the range of 9.5 to 12.5 in the presence of an oxidised hydroquinone a cyclisation reaction takes place cleaving the moiety -G-X from the remainder of the molecule and forming a cyclic structure comprising atoms of the moiety -G-X in which X represents

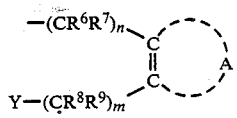

in which:
$R^6$ to $R^9$ are independently selected from H, alkyl of up to 12 carbon atoms or aryl of up to 12 carbon atoms,
A represents the necessary atoms to complete a benzene ring which may possess substituents,
Y represents OH, and
n is 0 or 1, m is 0 or 1 and (n+m) is 1 or 2 with the proviso that the formula excludes 1(2'-hydroxymethylbenzoyl)-2-phenylhydrazine.

6. The compound of claim 5 in which -GX represents

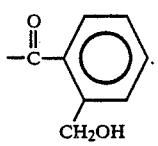

7. A hydrazine compound of the general formula

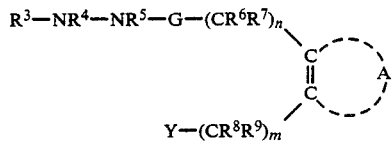

in which:

$R^3$ represents an aryl group or an aryl group with one or more non-electron withdrawing substituents, one of $R^4$ and $R^5$ is a hydrogen and the other is selected from hydrogen, aryl sulphonyl and trifluoroacetyl, G represents carbonyl,

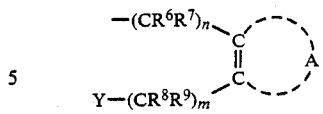

is X, a moiety such that at a pH in the range of 9.5 to 12.5 in the presence of an oxidised hydroquinone a cyclisation reaction takes place cleaving the moiety -G-X from the remainder of the molecule and forming a cyclic structure comprising atoms of the moiety -G-X, $R^6$ to $R^9$ are independently selected from H, alkyl of up to 12 carbon atoms or aryl of up to 12 carbon atoms, A represents the necessary atoms to complete a benzene ring which may possess substituents, Y represents OH, and n is 0 or 1, m is 0 or 1 and (n+m) is 1 or 2 with the proviso that the formula excludes 1(2'-hydroxymethylbenzoyl)-2-phenylhydrazine.

8. The compound of claim 7 in which -GX represents

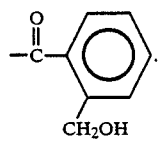

9. The compound of claim 7 wherein $R^3$ represents a phenyl group and A represents the atoms necessary to complete a phenyl group.

* * * * *

UNITED STATES PATENT AND TRADEMARK OFFICE
CERTIFICATE OF CORRECTION

PATENT NO. : 4,925,832
DATED      : May 15, 1990
INVENTOR(S): Hall and Mott

It is certified that error appears in the above-identified patent and that said Letters Patent is hereby corrected as shown below:

Column 10, Compound 4, line 14, "  "

should be -- 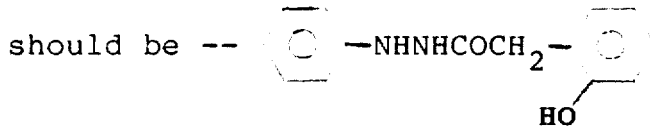

Column 11, line 48, "(2-hydoxy--b 4-6-dichloro-1,3,5-" should be -- (2-hydroxy-4-6 dichloro-1,3,5- --.

Signed and Sealed this

Twenty-ninth Day of October, 1991

Attest:

HARRY F. MANBECK, JR.

*Attesting Officer*  *Commissioner of Patents and Trademarks*